(12) United States Patent
Hud et al.

(10) Patent No.: US 6,677,158 B2
(45) Date of Patent: Jan. 13, 2004

(54) METHOD FOR MEASUREMENT OF GLYCATED HEMOGLOBIN BY A RAPID STRIP TEST PROCEDURE

(75) Inventors: Elizabeth A. Hud, Philadelphia, PA (US); Clyde W. Shearman, West Chester, PA (US); Van-Yu Wu, Cherry Hill, NJ (US)

(73) Assignee: Exocell Inc., Philadelphia, PA (US)

( * ) Notice: Subject to any disclaimer, the term of this patent is extended or adjusted under 35 U.S.C. 154(b) by 351 days.

(21) Appl. No.: 09/805,615

(22) Filed: Mar. 14, 2001

(65) Prior Publication Data

US 2002/0164811 A1 Nov. 7, 2002

(51) Int. Cl.[7] .............................. G01N 33/72; G01N 1/18
(52) U.S. Cl. ........................... 436/67; 436/66; 436/164; 436/165; 436/169; 436/170; 436/177; 436/178; 422/55; 422/56; 422/58; 422/60; 422/61; 422/101
(58) Field of Search .............................. 436/63, 66, 67, 436/164, 165, 166, 169, 170, 177, 178; 422/55, 56, 58, 60, 61, 101; 435/2

(56) References Cited

U.S. PATENT DOCUMENTS 5,695,949 A * 12/1997 Galen et al. .................. 435/14
6,162,645 A * 12/2000 Lee et al. ..................... 436/67
6,316,265 B1 * 11/2001 Lee et al. ..................... 436/67
6,399,293 B1 * 6/2002 Pachl et al. ................... 435/4
2003/0068830 A1 * 4/2003 McCroskey et al. ......... 436/518

FOREIGN PATENT DOCUMENTS

| GB | 2206411 | * | 1/1989 |
| WO | 92/08984 | * | 5/1992 |
| WO | 93/18407 | * | 9/1993 |
| WO | 95/34815 | * | 12/1995 |
| WO | 99/22242 | * | 5/1999 |

OTHER PUBLICATIONS

Bisse & Wieland:, Coupling of m–aminophenylboronic acid to s–triazine–activated Sephacryl: use in the affinity chromatography of glycated hemoglobins, J. Chromat 575:223, 1992.
Abraham et al., Application of affinity chromatography for separation and quantitation of glycosylated hemoglobins, J Lab Clin Med 102:187 1983.
Brownless et al. Measurement of Glycosylated Amino Acids and Peptides from Urine of Diabetic Patients Using Affinity Chromatogrpahy, Brownlee et al. Diabetes, 29:1044, 1980.

* cited by examiner

*Primary Examiner*—Maureen M. Wallenhorst

(57) ABSTRACT

The present invention is directed to a novel method for measurement of glycated hemoglobin, as well as assay methods and processes that can be used outside the medical laboratory setting to determine the fraction of total hemoglobin that is glycated.

10 Claims, No Drawings

US 6,677,158 B2

METHOD FOR MEASUREMENT OF GLYCATED HEMOGLOBIN BY A RAPID STRIP TEST PROCEDURE

TECHNICAL FIELD OF INVENTION

The present invention relates to a novel method for measurement of glycated hemoglobin, which is useful in the monitoring of glycemic control in people with diabetes, that can be performed without sample pretreatment and employed outside of the medical laboratory setting. The fraction of total hemoglobin that is glycated can be directly read by utilization of the method and device of the present invention.

BACKGROUND OF THE INVENTION

Glycated hemoglobin is the product of a nonenzymatic reaction resulting from the condensation of free glucose with reactive protein amino groups in the hemoglobin molecule. The amount of glycated hemoglobin in a person's blood reflects the average blood glucose concentration to which hemoglobin has been exposed during the life of erythrocytes in the circulation. Thus, in people with diabetes in whom glucose concentrations are elevated, the fraction of total hemoglobin that becomes glycated is increased. Measurement of glycated hemoglobin is useful in monitoring glycemic control in diabetic patients. Typically, a blood sample is obtained from the patient during a visit to the physician and is sent to a medical laboratory which determines the glycated hemoglobin level by one of several methods known in the art.

Methods described to measure glycated hemoglobin include column chromatography on ion exchange or affinity resins, high pressure liquid chromatography (HPLC), agarose gel electrophoresis, and immunochemical assays. Each of these has drawbacks with respect to complexity, need for costly instrumentation, accuracy, specificity or other factors, and none is suited to performance by the nontechnically trained or by the patient himself or herself. Periodic measurement of glycated hemoglobin is a mainstay in the management of patients with diabetes, who are becoming increasingly aware of the importance of glycemic control in forestalling the development of vascular and other complications of diabetes. To that end, diabetic patients are advised to regularly measure their own blood glucose concentrations, using procedures referred to as home-glucose monitoring. Such procedures allow the individual to self-assess his/her blood glucose outside of the medical laboratory setting, at any time, and as frequently as deemed advisable. Typically these procedures entail application of a drop of blood to a device that is fashioned so as to provide, by chemical or electrochemical reaction, a colored or other read-out signal that relates to the glucose concentration and can be read visually or by simple, hand-held instrumentation. There is presently no existing product that allows diabetic patients to self-assess their own glycated hemoglobin levels.

It would therefore be desirable to be able to quantify the amount of glycated hemoglobin with a method that can be performed outside of the medical laboratory setting by nontechnically trained people such as persons with diabetes, since such measurement would provide the individual with an immediate assessment of the average ambient blood glucose concentration during the preceding weeks and, therefore, an indication of need for adjustment in anti-diabetic therapy.

Various reagents are known to bind carbohydrate residues such as glucose that are linked to proteins, including conconavalin A and other lectins. Boronate reagents have been found to form 1, 2-cis-diol complexes with glucose residues in glycated proteins (Brownlee et al, Diabetes 29:1044, 1980; Abraham et al, J Lab Clin Med 102: 187, 1983; Olufemi et al, Clin Chim Acta 163:125, 1987). Most investigations have employed protein or sugar binding reagents such as DEAE or boronic acid covalently bound to carriers such as aminoethyl cellulose, polyacrylamide, agarose and Sepharose (Weith et al, Biochemistry 9:4396, 1970; Pace & Pace, Anal Biochem 107:128, 1980). These carriers have various disadvantages such as nonspecific adsorption, flow characteristics, residual charge, binding capacity, hydrophobic groups, molecular mass exclusion, and swelling or shrinking with changes in pH or ionic strength. All of them require a series of adsorption/elution steps with different solutions and collection of resultant liquid fractions and assaying for the amount of the protein of interest in these fractions. For determination of glycated hemoglobin, all of them require pretreatment of the sample before the method is initiated in order to release hemoglobin from erythrocytes, and none of them allow direct application of a blood sample to the carrier for separation of glycated from nonglycated hemoglobin. Phenylboronic acid coupled to a cross-linked co-polymer of allyl dextran with N, N-methylenebisacrylamide has been noted to have potential advantages over other carriers because of enhanced stability and greater pressure handling capacity for fast protein liquid chromatography (FPLC) applications (Bisse & Wieland, J Chromatog 575:223, 1992). However, utilization of this carrier for separation of glycated and nonglycated hemoglobins also requires column chromatography with a complex adsorption/elution scheme; additionally, before application to the column, the blood sample must be centrifuged to separate erythrocytes from plasma, and the erythrocytes must be washed several times and hemolysed. The present invention, in contrast, affords the novel and improved features of eliminating the need for any column chromatography apparatus or procedure or for any collection of liquid fractions, and allowing implementation of the method without any pretreatment of the blood sample, which can be directly applied.

Coupling of protein or sugar binding reagents such as DEAE or boronate to matrices is known in the art (U.S. Pat. No. 4269605). A general method for coupling of aminophenylboronic acid to a sephacryl matrix is known to those skilled in the art (Bisse & Wieland 575:223, 1992). A novel and improved adaptation of these principles entails the immobilization of boronate reagent or DEAE reagent onto a paper support wherein the separation of glycated and non-glycated hemoglobins is effectuated in situ without the need for elution and liquid collection steps, and the sample is applied directly, without pretreatment, to initiate the separation. This is accomplished by incorporating the principle of fluid flow, a version of which has been applied in solid phase immunoassay procedures, wherein anti-analyte antibodies that are immobilized onto a solid phase support capture the desired analyte and said capture is detected with the addition of a colored tracer or carrier (U.S. Pat. No. 5,798,273). The present invention provides the novel adaptation of this principle wherein the immobilized reagent is non-antibody/non-proteinaceous, and the detection of captured analyte does not require the addition of colored tracer or carrier for read-out.

SUMMARY OF THE INVENTION

The present invention provides a novel method for measurement of glycated hemoglobin that can be performed outside of the medical laboratory setting, affords results rapidly, and can be conveniently performed by nontechnically trained individuals at any place or time, including the home.

The invention provides a novel method for separating glycated from nonglycated hemoglobin utilizing a test strip device to achieve chemical complexation of glycated hemoglobin and eliminating the need for column chromatography.

Additionally the invention provides a novel method and device for directly measuring the fraction in an applied sample of total hemoglobin that is glycated.

The invention further provides a novel method by which glycated hemoglobin can be determined without pretreatment of the blood sample before implementation of the procedure.

The method comprises immobilization of a glycated hemoglobin binding reagent onto activated porous material, applying a sample of blood to a conjoined application pad, and dispersing the applied sample onto the glycated hemoglobin binding membrane by fluid flow after the addition of a small volume of buffer solution. The glycated hemoglobin binding membrane forms complexes with glucose residues contained in glycated hemoglobin, causing their retention, whereas nonglycated hemoglobin is not retained and proceeds to migrate through the glycated hemoglobin binding membrane and into a nonglycated hemoglobin binding membrane, where it is trapped. Untrapped material then flows into an end-piece wicking membrane.

DETAILED DESCRIPTION OF THE INVENTION

The present invention is directed to a method and device for measurement of glycated hemoglobin that allows rapid results without the use of column chromatography or complicated separatory procedures. This method utilizes the principles of specific chemical complexation and of fluid flow to distinguish glycated from nonglycated species of hemoglobin in a strip test system in which an immobilized chemical reagent binds to and retains the glycated hemoglobin species. The reagent complexes with glucose residues which are present in glycated hemoglobin and absent in nonglycated hemoglobin.

In a preferred embodiment of the present invention, a whole blood sample (i.e. blood containing formed elements and plasma) is placed onto an application pad, following which a solution that lyses the erythrocytes contained in the sample is added to the application slot. The hemoglobin liberated from sample erythrocytes disperses into the applied solution and the mixture enters the application pad by flow of the fluid. The hemoglobin then flows into a conjoined porous membrane which has been derivatized with a glycated hemoglobin binding reagent. The glycated hemoglobin in the sample is retained by this membrane and the nonglycated hemoglobin flows through into a conjoined membrane that binds the nonglycated hemoglobin. Finally, any unbound material flows into a conjoined wicking membrane. The completed solid support therefore contains four specific sequentially conjoined porous membrane areas consisting of: 1) A sample application pad; 2) A glycated hemoglobin binding membrane; 3) A nonglycated hemoglobin binding membrane; 4) A buffer flow wicking membrane.

The higher the fraction of total hemoglobin that is glycated in a sample, the greater the proportion of hemoglobin in an applied sample that will be retained by the glycated hemoglobin binding membrane. Trapping and measuring the nonglycated hemoglobin that is not retained in the glycated hemoglobin binding membrane internally controls for application, lysing and migration characteristics of individual samples such that the hemoglobin in the glycated versus the nonglycated areas provides a measure of the fraction of applied hemoglobin that is glycated. The intrinsic red color of hemoglobin affords read-outs in the glycated and nonglycated areas that can be readily determined. Importantly, it is not necessary to add a reagent containing a tracer such as colored particles that would attach to the glycated or nonglycated hemoglobin species in order to detect and quantitate these fractions with the present invention.

A preferred embodiment of the device of the present invention is a solid support which contains four sequentially conjoined porous membrane areas consisting of: a sample application pad, a glycated hemoglobin binding membrane, a nonglycated hemoglobin binding membrane and a buffer flow wicking membrane. The application pad which is employed in the assay is generally a filter paper, with a synthetic polymer grade filter paper giving exceptionally good results. Although synthetic polymer grade paper is a preferred material for producing the application pad, it is to be understood that other materials may also be employed for producing such application pads including but not limited to cellulose acetate, rayon, cotton linter, nylon, PVDF, glass fiber and nitrocellulose. The glycated hemoglobin binding membrane which is employed in the assay is generally a porous material derivatized with glycated hemoglobin binding molecules. Activated cotton linter paper is a preferred material for the glycated hemoglobin binding membrane, but it is to be understood that other materials may also be employed including but not limited to rayon, cotton, cellulose, cellulose acetate, nylon, glass fiber and nitrocellulose. A preferred glycated hemoglobin binding molecule is amino phenylboronate. It is to be understood that other molecules may also be employed including but not limited to concanavalin A, broad bean lectin, Vicia sativa lectin, sweet pea lectin, Lentil lectin, Jack bean lectin and glycation specific antibodies. The nonglycated hemoglobin binding membrane which is employed in the assay is generally a porous material capable of binding hemoglobin or derivatized with hemoglobin binding molecules. Glass fiber paper is a preferred material for the nonglycated hemoglobin membrane, but it is to be understood that other materials may be employed including but not limited to cellulose, cellulose acetate, rayon, cotton, nylon, PVDF, cotton linter and nitro- cellulose. A preferred nonglycated hemoglobin binding molecule is glass fiber or diethylaminoethyl (DEAE). It is to be understood that other molecules may also be employed including but not limited to positively charged groups such as trinary alkylamines, quaternary alkylamines, quaternary alkyl alkanolamines, quaternary ammonium, polyamines, and alkylamines; negatively charged groups such as carboxylic acids and sulfonic acids; hydrophobic groups such as aromatic, acrylic, hydroxyapatite, silica, alumina, and alkyl; and affinity reagents such as hemoglobin antibodies and wheat protease. The buffer flow wicking membrane which is employed in the assay is generally a porous material, with cotton linter paper giving very good results. It is to be understood that other materials may also be employed for producing paper membranes including but not limited to cellulose, cellulose acetate, rayon, cotton, nylon, PVDF, glass fiber and nitrocellulose.

Another preferred embodiment of the device of the present invention is a housing into which the solid support is inserted (such as, for example, a plastic housing). The housing has a top frame having a hole located over the application pad, a window located over the glycated hemoglobin binding membrane and a window over the nonglycated hemoglobin binding membrane. A section of the application pad can be seen through the hole and a section of the glycated hemoglobin binding membrane and a section of the nonglycated hemoglobin binding membrane can be seen through their respective windows.

The above disclosure generally describes the present invention. A more complete understanding can be obtained by reference to the following specific examples which are provided herein for purposes of illustration only and are not intended to limit the scope of the invention.

EXAMPLE 1

Activation of Paper

A 17.5×7.5 cm rectangle of paper (Schleicher & Schuell #470) was immersed in a solution of 2M sodium hydroxide for 15 minutes at room temperature. The paper was lifted from the solution, excess liquid discarded, and reimmersed in 10 ml of cold sodium hydroxide (4° C.) and cooled to 0° C. in an ice bath. Two grams of cyanuric acid were dissolved in 20 ml of chloroform, filtered, the filtrate discarded, and the solid was redissolved into 20 ml of pre-cooled acetone. This solution was then added to the paper and the mixture continuously stirred for 70 min. in an ice bath, followed by 30 min. of stirring at room temperature. The paper was removed from the solution, excess liquid drained, and was rinsed three times with 50 ml of 50% (v/v) acetic acid/water and then with water (250 ml).

EXAMPLE 2

Coupling of Amino-phenylboronic Acid to Activated Paper

The activated paper was immersed in 10 ml of coupling buffer (0.2M $K_2HPO_4$/0.2M $KH_2PO_4$; 8.5:1.5 v/v; pH 7.6), to which was added 20 ml of coupling buffer containing 5 mg/ml aminophenylboronic acid hemisulphate. The mixture was stirred by shaking for 12 hours at room temperature. The paper was then repeatedly washed thoroughly with coupling buffer. The derivatized paper was then immersed in 20 ml of coupling buffer containing 0.25M ethanolamine and stirred 4–5 hours at room temperature. It was again washed with coupling buffer followed by 0.2M sodium acetate, pH 4.5, and finally washed with distilled water and air dried.

EXAMPLE 3

Mounting the Derivatized Paper

The boronate derivatized paper designated the glycated hemoglobin binding membrane was cut into strips measuring approximately 0.4×1.0 cm. One end of the cut strip was conjoined to a 0.4×2.0 cm strip of synthetic polymer (Schleicher & Schuell #8-S) designated the application pad. The opposite end was conjoined to a 0.4×1.0 cm strip of glass fiber paper (Whatman GF/DVA) designated the nonglyeated hemoglobin binding membrane, which in turn was conjoined to a 0.4×1.0 cm strip of synthetic polymer paper designated the buffer flow wicking membrane (S & S #470). Conjoining of the four membrane strips into a solid support system was accomplished by applying the pieces to an adhesive coated strip of vinyl (0.4×5.0 cm), such that they were in fluid contact with each other.

EXAMPLE 4

Sample Application and Method Initiation

An aliquot (1 $\mu$L) of whole blood, collected by finger prick into a capillary tube treated with anti-coagulant, was applied to the application pad. Three drops, each approximately 40 $\mu$L, of lysing/migration buffer (0.75% DL-asparagine, 1.25% L-methionine, 0.746% taurine, 2.032% $MgCl_2$ [w/v], 0.5% Tween 20 [v/v], pH 9.0) were added in dropwise fashion to the application slot.

EXAMPLE 5

Execution and Readout

Addition of buffer as in Example 4 lysed the erythrocytes in the blood sample that had been applied and initiated by fluid flow the migration of the hemoglobin contained within the erythrocytes from the application pad into the glycated hemoglobin binding membrane. Migration proceeded by fluid flow through the glycated hemoglobin binding membrane, then into the nonglycated hemoglobin binding membrane, and finally into the buffer flow wicking membrane. Glycated hemoglobin was retained by complexation-adsorption to the glycated hemoglobin binding membrane, whereas the nonglycated hemoglobin did not complex and was not retained by the glycated hemoglobin binding membrane, allowing it to migrate through to the nonglycated hemoglobin binding membrane where it was bound. The intensities of the red color of the hemoglobin in the glycated hemoglobin binding membrane and in the nonglycated hemoglobin binding areas were read. The ratio of color intensity in the glycated to the nonglycated hemoglobin binding areas provided a measure of the fraction of total hemoglobin in the sample that is glycated.

EXAMPLE 6

1–2 $\mu$L of blood sample from subjects with different concentrations of glycated hemoglobin, measured by high pressure liquid chromatography (HPLC), were applied to mounted solid supports prepared as described in Examples 1–4, and subjected to the method for determination of glycated hemoglobin performed as described in Examples 4 and 5.

| | | Binding Area Color Intensity | | |
|---|---|---|---|---|
| Sample | % Glycated by HPLC | Glycated Hemoglobin | Nonglycated Hemoglobin | % Glycated Hbg by Invention Method |
| 1 | 4.5 | 0.09 | 1.8 | 4.8 |
| 2 | 6.0 | 0.13 | 2.0 | 6.1 |
| 3 | 8.5 | 0.18 | 1.9 | 8.6 |
| 4 | 11.0 | 0.28 | 2.2 | 11.3 |

What is claimed is:

1. A method for determining glycated hemoglobin in a test sample, comprising the steps of:
   a. applying a test sample of whole blood in which there are erythrocytes containing red-colored glycated and non-glycated hemoglobins to an application pad, wherein the application pad receives the test sample and is in fluid flow contact with a first capture site comprising a first porous material to retain substantially all of the glycated hemoglobin;
   b. adding a solution to the application pad to disrupt erythrocytes in the applied sample, releasing hemoglobin from the erythrocytes and causing by fluid flow the released hemoglobin to disperse into the application pad and subsequently onto the first capture site;
   c. permitting the first capture site to retain substantially all of the glycated hemoglobin;

d. flowing the test sample from the first capture site to a second capture site, the second capture site being in fluid flow contact with the first capture site, the second capture site comprising a second porous material that retains substantially all of the non-glycated hemoglobin;

e. permitting the second capture site to retain substantially all of the non-glycated hemoglobin;

f. flowing the test sample and residual solution from the second capture site to an end-piece wicking membrane, the end-piece wicking membrane being in fluid flow contact with the second capture site, the end-piece wicking membrane comprising a third porous material;

g. reading the intensity of the red color intrinsic to both glycated and non-glycated hemoglobin in the first and second capture sites with no requirement for additional colored tracer or reagent for readout; and h. determining a ratio of the amount of glycated hemoglobin in the first capture site to the amount of non-glycated hemoglobin in the second capture site.

2. The method of claim 1 additionally comprising the step of selecting the first porous material to additionally comprise immobilized sugar binding molecules.

3. The method of claim 2 additionally comprising the step of selecting the sugar binding molecules to additionally comprise phenylboronic acid.

4. The method of claim 1 additionally comprising the step of selecting the second porous material to additionally comprise immobilized protein binding molecules.

5. The method of claim 4 additionally comprising the step of selecting the protein binding molecules to additionally comprise diethylaminoethyl.

6. The method of claim 1 additionally comprising the step of selecting the application pad to additionally comprise cellulose, rayon, cotton, cellulose acetate, glass fiber, nylon, nitrocellulose, cotton linter, or Polyvinylidene Fluoride.

7. The method of claim 6 additionally comprising the step of selecting the application pad to additionally comprise a synthetic polymer grade filter paper.

8. The method of claim 1 additionally comprising the step of selecting the first porous material to additionally comprise phenylboronate, lectins such as concanavalin A, broad bean lectin, Vicia sativa lectin, sweet pea lectin, Jack bean lectin, and lentil lectin, or glycation specific antibodies.

9. The method of claim 1 additionally comprising the step of selecting the second porous material to additionally comprise glass fiber, diethylaminoethyl, positively charged groups such as trinary alkylamines, quaternary alkylamines, quatemary alkyl alkanolamines, quaternary ammonium, polyamines and alkylamines; negatively charged groups such as carboxylic acids and sulfonic acids; hydrophobic groups such as aromatic, acrylic, hydroxyapatite, silica, alumina and alkyl; and affinity reagents such as hemoglobin antibodies and wheat protease.

10. The method of claim 1 additionally comprising the step of selecting the third porous material to additionally comprise cotton linter.

* * * * *